United States Patent
Abolfathi et al.

(10) Patent No.: US 7,361,020 B2
(45) Date of Patent: Apr. 22, 2008

(54) DENTAL TRAY CONTAINING RADIOPAQUE MATERIALS

(75) Inventors: Amir Abolfathi, Menlo Park, CA (US); Loc X. Phan, San Jose, CA (US); Robert E. Tricca, Danville, CA (US)

(73) Assignee: Align Technology, Inc., Santa Clara, CA (US)

( * ) Notice: Subject to any disclaimer, the term of this patent is extended or adjusted under 35 U.S.C. 154(b) by 398 days.

(21) Appl. No.: 10/717,798

(22) Filed: Nov. 19, 2003

(65) Prior Publication Data

US 2005/0106528 A1 May 19, 2005

(51) Int. Cl.
*A61C 11/00* (2006.01)
*A61C 9/00* (2006.01)

(52) U.S. Cl. .................. 433/213; 433/214; 433/48

(58) Field of Classification Search ............... 433/213, 433/37, 38, 39, 40–48, 214
See application file for complete search history.

(56) References Cited

U.S. PATENT DOCUMENTS

| | | | |
|---|---|---|---|
| 53,347 A | 3/1866 | Schaffer | |
| 98,066 A | 12/1869 | Jenks | |
| 1,489,192 A | 4/1924 | Cleveland | |
| 1,499,482 A | 7/1924 | Simmons | |
| 1,652,910 A | 12/1927 | Psayla | |
| 2,467,432 A | 4/1949 | Kesling | |
| 2,594,832 A | 4/1952 | Wentzel | |
| 2,685,137 A | 8/1954 | Thompson | |
| 2,860,414 A | 11/1958 | Brant | |
| 3,574,259 A | 4/1971 | Jones | |
| 3,626,594 A | 12/1971 | Zinner et al. | |
| 3,660,900 A | 5/1972 | Andrews | |
| 3,860,803 A | 1/1975 | Levine | |
| 3,878,610 A * | 4/1975 | Coscina | 433/37 |
| 3,916,526 A | 11/1975 | Schudy | |
| 3,950,851 A | 4/1976 | Bergersen | |
| 3,978,585 A | 9/1976 | Holcomb | |
| 3,987,548 A | 10/1976 | Jones | |
| 4,014,096 A | 3/1977 | Dellinger | |
| 4,145,812 A | 3/1979 | Johnson et al. | |
| 4,195,046 A | 3/1980 | Kesling | |
| 4,324,546 A | 4/1982 | Heitlinger et al. | |
| 4,348,178 A | 9/1982 | Kurz | |
| 4,368,040 A | 1/1983 | Weissman | |
| 4,375,966 A * | 3/1983 | Freeman | 433/37 |

(Continued)

FOREIGN PATENT DOCUMENTS

AT 149778 5/1937

(Continued)

OTHER PUBLICATIONS

Alexander et al., "The DigiGraph Work Station Part 2, Clinical Management," *JCO* (Jul. 1990), pp. 402-407.

(Continued)

*Primary Examiner*—Cary E. O'Connor

(57) ABSTRACT

A method to create a digital model of a patient's teeth includes taking an impression of the patient's teeth using a radiopaque dental tray; scanning the impression and the dental tray using a dental tray containing a radiopaque agent; scanning the impression and the dental tray using a radiographic source; and generating the digital model with scanned data.

38 Claims, 7 Drawing Sheets

U.S. PATENT DOCUMENTS

| | | |
|---|---|---|
| 4,432,728 A | 2/1984 | Skarky |
| 4,478,580 A | 10/1984 | Barrut |
| 4,504,225 A | 3/1985 | Yoshii |
| 4,505,673 A | 3/1985 | Yoshii |
| 4,575,805 A | 3/1986 | Moermann et al. |
| 4,611,288 A | 9/1986 | Duret et al. |
| 4,656,860 A | 4/1987 | Orthuber et al. |
| 4,663,720 A | 5/1987 | Duret et al. |
| 4,689,010 A | 8/1987 | Wolfe |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,837,732 A | 6/1989 | Brandestini et al. |
| 4,850,864 A | 7/1989 | Diamond |
| 4,856,991 A | 8/1989 | Breads et al. |
| 4,936,862 A | 6/1990 | Walker et al. |
| 4,937,928 A | 7/1990 | Van Der Zel |
| 4,964,770 A | 10/1990 | Steinbichler et al. |
| 4,975,052 A | 12/1990 | Spencer et al. |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,040,976 A | 8/1991 | Ubel, III et al. |
| 5,055,039 A | 10/1991 | Abbatte et al. |
| 5,059,118 A | 10/1991 | Breads et al. |
| 5,064,371 A | 11/1991 | Smeltzer |
| 5,076,785 A | 12/1991 | Tsai |
| 5,100,316 A | 3/1992 | Wildman |
| 5,121,333 A | 6/1992 | Riley et al. |
| 5,128,870 A | 7/1992 | Erdman et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,297,960 A | 3/1994 | Burns |
| 5,336,086 A | 8/1994 | Simmen et al. |
| 5,338,198 A | 8/1994 | Wu et al. |
| 5,340,308 A | 8/1994 | Cukjati |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,503,497 A | 4/1996 | Dudley et al. |
| 5,513,985 A | 5/1996 | Robertson |
| 5,518,397 A | 5/1996 | Andreiko et al. |
| 5,533,895 A | 7/1996 | Andreiko et al. |
| 5,542,842 A | 8/1996 | Andreiko et al. |
| 5,549,476 A | 8/1996 | Stern |
| 5,551,872 A | 9/1996 | Mena |
| 5,580,244 A | 12/1996 | White |
| 5,582,488 A | 12/1996 | Dudley et al. |
| 5,587,912 A | 12/1996 | Andersson et al. |
| 5,605,459 A | 2/1997 | Kuroda et al. |
| 5,607,305 A | 3/1997 | Andersson et al. |
| 5,636,985 A | 6/1997 | Simmen et al. |
| 5,645,421 A | 7/1997 | Slootsky |
| 5,655,653 A | 8/1997 | Chester |
| 5,683,243 A | 11/1997 | Andreiko et al. |
| 5,733,118 A | 3/1998 | Pankuch et al. |
| 5,733,126 A | 3/1998 | Andersson et al. |
| 5,740,267 A | 4/1998 | Echerer et al. |
| 5,890,895 A | 4/1999 | Tucker |
| 5,975,893 A | 11/1999 | Chishti et al. |
| 6,071,121 A | 6/2000 | Simon |
| 6,428,315 B1 | 8/2002 | Prestipino et al. |
| 6,540,516 B1* | 4/2003 | Ziegler ................. 433/214 |
| 6,629,841 B1 | 10/2003 | Skinner |
| 2002/0094509 A1* | 7/2002 | Durbin et al. ........... 433/213 |
| 2002/0156186 A1* | 10/2002 | Bublewitz et al. ........ 525/100 |
| 2003/0129565 A1* | 7/2003 | Kaza ..................... 433/213 |

FOREIGN PATENT DOCUMENTS

| | | |
|---|---|---|
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0774933 B1 | 5/1997 |
| EP | 0541500 A1 | 6/1998 |
| EP | 0731673 B1 | 9/1998 |
| FR | 737739 | 12/1932 |
| FR | 2369828 A1 | 6/1978 |
| FR | 2652256 A1 | 3/1991 |
| IT | 417420 | 1/1947 |
| WO | WO 90/08512 A1 | 8/1990 |
| WO | WO 91/04713 A1 | 4/1991 |
| WO | WO 92/03985 | 3/1992 |
| WO | WO 94/10935 A1 | 5/1994 |
| WO | WO 98/44865 A1 | 10/1998 |
| WO | WO 98/58596 A1 | 12/1998 |

OTHER PUBLICATIONS

Altschuler et al, "Measuring Surfaces Space-Coded by a Laser-Projected Dot Matrix," *SPIE Imaging Applications for Automated Industrial Inspection and Assembly*, vol. 182 (1979), p. 187-191.

Altschuler et al., "Analysis of 3-D Date for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.

Altschuler et al., "Laser Electro-Optic System for Rapid Three-Dimensional (3D) Topographic Mapping of Surfaces," *Optical Engineering*, vol. 20(6) (1981), pp. 953-961.

Altschuler, "3D Mapping of Maxillo-Facial Prosthesis," AADR Abstract #607, 1980, 1 page total.

American Association for Dental Research, Summary of Activities, Mar. 20-23, 1980, Los Angeles, CA, p. 195.

Andersson et al., "Clinical Results with Titanium Crowns Fabricated with Machine Duplication and Spark Erosion," *Acta Odontological Scandinavia*, vol. 47 (1989), pp. 279-286.

Baumrind et al., "A Stereophotogrammetric System for the Detection of Prosthesis Loosening in Total Hip Arthroplasty, NATO Symposium on Applications of Human Biostereometrics, Jul. 9-13, 1978," SPIE vol. 166, pp. 112-123.

Baumrind et al., Mapping the Skull in 3-D, Reprinted from The Journal, *California Dental Association*, vol. 48, No. 2 (1972) Fall Issue) 11 pages total.

Baumrind, "A System for Craniofacial Mapping Through the Integration of Data from Stereo X-Ray Films and Stereo Photographs," An invited paper submitted to the 1975 American Society of Photogram. Symposium on Close-Range Photogram. Systems, University of Ill., Aug. 26-30, 1975, pp. pp. 142-166.

Baumrind, "Integrated Three-Dimensional Craniofacial Mapping: Background, Principles, and Perspectives," *Seminars in Orthodontics*, vol. 7, No. 4 (Dec. 2001), pp. 223-232.

Begole et al., "A Computer System for the Analysis of Dental Casts," *The Angle Orthodontist*, vol. 51 No. 3 (Jul. 1981), pp. 253-259.

Bernard et al., "Computerized Diagnosis in Orthodontics for Epidemiological Studies: A Progress Report", Abstracts of Papers, *Journal of Dental Research*; vol. 67, Special Issue Mar. 9-13, 1988, p. 169.

Bhatia et al., "A Computer-Aided Design for Orthognathic Surgery," *British Journal of Oral and Maxillofacial Surgery*, vol. 22 (1984), pp. 237-253.

Biggerstaff et al., "Computerized Analysis of Occlusion in the Postcanine Dentition," *American Journal of Orthodontics*, vol. 61, No. 3 (Mar. 1972), pp. 245-254.

Biggerstaff, "Computerized Diagnostic Setups and Simulations," *The Angle Orthodontist*, vol. 40, No. 1 (Jan. 1970), pp. 28-36.

Boyd et al., "Three Dimensional Diagnosis and Orthodontic Treatment of Complex Malocclusions Wlith the Invisalign Appliance", *Seminars in Orthodontics*, vol. 7, No. 4 (Dec. 2001), p. 274-293.

Brandestini et al. "Computer Machined Ceramic Inlays: In Vitro Marginal Adaptation," *Journal of Dental Research*, vol. 64/Special Issue/Abstracts, IADR/AADR Abstracts 1985, p. 208.

Brook et al., An Image Analysis System for the Determination of Tooth Dimensions from Study Casts: Comparison with Manual Measurements of Mesio-distal Diameter, *J Dent Res.*, vol. 65, No. 3, Mar. 1986, pp. 428-431.

Burstone (interview), "Dr. Charles J. Burstone on The Uses of the Computer in Orthodontic Practice (Parts 1 and 2)," *Journal of Clinical Orthodontics*, (Part 1) vol. 8, No. 7 , Jul. 1979; (Part 2) vol. 8, No. 8 pp. 539-551, Aug. 1979.

Burstone et al., "Precision Adjustment of the Transpalatal Lingual Arch: Computer Arch Form Predetermination," *Am. Journal of Orthodontics*, vol. 79, No. 2 (Feb. 1981), pp. 115-133.

Chaconas et al., "The DigiGraph Work Station, Part 1, Basic Concepts," *JCO* (Jun. 1990), pp. 360-367.

Chafetz et al., "Subsidence of the Fermoral Prosthesis, A Stereophotogrammetric Evaluation," *Clinical Orthopaedics and Related Research*, No. 201 (Dec. 1985), pp. 60-67.

Chiappone, "Constructing the Gnathologic Setup And Positioner" *J. Clin. Orthod.*, 14:121-133, 1980.

Cottingham, "Gnathologic Clear Plastic Positioner" *Am. J. Orthod.*, vol. 55, No. 1, (Jan. 1969),. pp. 23-31.

Crawford, "Computers in Dentistry: Part 1: CAD/CAM: The Computer Moves Chairside," "Part 2: F. Duret—A Man With A Vision," "Part 3: The Computer Gives New Vision- Literally," "Part 4: Bytes 'N Bites" The Computer Moves From The Front Desk To The Operatory, *Canadian Dental Journal*, vol. 54(90, , (1988), pp. 661-666.

Crawford, "CAD/CAM in the Dental Office: Does It Work?" *Canadian Dental Journal*, vol. 57, No. 2 (Feb. 1991), pp. 121-123.

Crooks, "CAD/CAM Comes to USC," *USC Dentistry*, (Spring 1990) pp. 14-17.

Cureton, "Correcting Malaligned Mandibular Incisors With Removable Retainers" *J. Clin. Orthod.*, 30:390-395, 1996.

Curry et al., "Integrated Three-Dimensional Craniofacial Mapping at the Craniofacial Research Instrumentation Laboratory/University of the Pacific," *Seminars in Orthodontics*, vol. 7, No. 4 (Dec. 2001), pp. 258-265.

Cutting et al., "Three-Dimensional Computer-Assisted Design of Craniofacial Surgical Procedures: Optimization and Interaction with Cephalometric and CT-Based Models," *Plastic Reconstructive Surgey*, vol. 77, No. 6 (Jun. 1986), pp. 877-885.

DCS Dental AG, "The CAD/CAM 'DCS Titan System' for Production of Crowns/Bridges" *DSC Production AG*, Jan. 1992, pp. 1-7.

Defranco et al., "Three-Dimensional Large Displacement Analysis of Orthodontic Appliances," *J. Biomechanics*, vol. 9 (1976), pp. 793-801.

Dental Institute University of Zurich Switzerland, Program for International Symposium on Computer Restorations: State of the Art of the CEREC-Method, May 1991, 2 pages total.

DenTrac Corporation, Dentrac document, pp. 4-13.

Duret et al., "CAD-CAM in Dentistry," *Journal of the American Dental Association*, vol. 117 (Nov. 1988), pp. 715-720.

Duret et al., "CAD/CAM Imaging in Dentistry," *Current Opinion in Dentistry*, vol. 1 (1991), pp. 150-154.

Duret, "Vers une prosthese informatisee," (English translation also attached), *Tonus*, vol. 75, (Nov. 15, 1985), pp. 55-57.

Duret, "The Dental CAD/CAM, General Description of the Project," *Hennson International Product Brochure*, Jan. 1986., 18 pages total.

Economides, "The Microcomputer in the Orthodontic Office," *JCO*, (Nov. 1979), pp. 767-772.

Elsasser, "Some Observations on the History and Uses of the Kesling Positioner" *Am. J. Orthod.*, vol. 36, No. 5, (May 1950) pp. 368-374.

Faber et al.,"Computerized interactive orthodontic treatment planning," *Am. J. Orthod.*, vol. 73, No. 1 (Jan. 1978), pp. 36-46.

Felton et al. "A computerized analysis of the shape and stability of mandibular arch form," *Am. Journal of Orthodontics and Dentofacial Orthopedics*, vol. 92, No. 6 (Dec. 1987), pp. 478-483.

Friede et al., "Accuracy of Cephalometric Prediction in Orthognathic Surgery," Abstract of Papers, *Journal of Dental Research*, vol. 70 (1987), pp. 754-760.

Gim-Alldent Deutschland, "Das DUX System: Die Technik" 2 pages total.

Grayson, "New Methods for Three Dimensional Analysis of Craniofacial Deformity," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. 1, Aug. 1990, p. 5-6.

Guess et al., "Computer Treatment Estimates in Orthodontics and Orthognathic Surgery,"*JCO*, (Apr. 1989), pp. 262-328.

Heaven et al., "Computer-based Image Analysis of Artificial Root Surgace Caries," Abstracts of Papers, *Journal of Dental Research*, vol. 70,Apr. 17-21, 1991, p. 528.

Hoffmann et al., "Role of Cephalometry for Planning of Jaw Orthopedics and Jaw Surgery Procedures," (Article Summary in English, article in German), *Informationen*, (Mar. 1991), pp. 375-396.

Huckins, "CAD-CAM Generated Mandibular Model Protoype from MRI Data," *AAOMS* 1999, p. 96.

JCO Interviews, "Craig Andreiko , DDS, MS on the Elan and Orthos Systems", JCO, (Aug. 1994), pp. 459-468.

JCO Interviews, "Dr. Homer W. Phillips on Computers in Orthodontic Practice, Part 2," JCO, (Dec. 1983), pp. 819-831.

Jerrold, "The Problem, Electronic Data Transmission and the Law," *AJO-DO*, (Apr. 1988), pp. 478-479.

Jones et al., "Assessment of the Fit of a Parabolic Curve to Pre- and Post-Treatment Dental Arches," *British Journal of Orthodontics*, vol. 16 (1989), pp. 85-93.

Kamada et al., "Case Reports on Tooth Positioners Using LTV Vinyl Silicone Rubber" J. Nihon University School of Dentistry, 26(1):11-29, 1984.

Kamada et al., "Construction of Tooth Positioners With LTV Vinyl Silicone Rubber and Some Case Reports" J. Nihon University School of Dentistry, 24(1):1-27, 1982.

Kanazawa et al., "Three-Dimensional Measurements of the Occlusal Surfaces of Upper Molars in a Dutch Population," *J. Dent Res.* , vol. 63, No. 11 (Nov. 1984), pp. 1298-1301.

Kesling, "Coordinating the Predetermined Pattern and Tooth Positioner With Conventional Treatment" *Am. J. Orthod. Oral. Surg.*, 32:285-293, 1946.

Kesling, "The Philosophy of the Tooth Positioning Appliance" *Am. J. Orthod. Oral. Surg.*, 31(6):297-304, 1945.

Kleemann et al., "The Speed Positioner" *J. Clin. Orthod.*, 30:673-680, 1996.

Kuroda et al., "Three-dimensional dental cast analyzing system using laser scanning" *Am. J. Orthod. Dentofac. Orthop.*, 110:365-369, 1996.

Laurendeau et al., "A Computer-Vision Technique for the Acquisition and Processing of 3-D Profiles of Dental Imprints: An Application in Orthodontics," *IEEE Transactions on Medical Imaging*, vol. 10, No. 3 (Sep. 1991), pp. 453-461.

Leinfelder et al., "A new method for generating ceramic restorations: a CAD-CAM system," *Journal Of The American Dental Assoc.*, vol. 118, No. 6 (Jun. 1989), pp. 703-707.

Manetti et al., "Computer-aided Cefalometry and New Mechanics in Orthodontics" (Article Summary in English, article in German), *Fortschr. Kieferorthop.* 44, 370-376 (Nr. 5), 1983.

McCann, Inside the ADA, *Journal Of The American Dental Assoc.*, vol. 118 (Mar. 1989) pp. 286-294.

McNamara et al., "Invisibl Retainers", *J. Clinical Orthodontics*, (Aug. 1985) pp. 570-578.

McNamara et al., Chapter 19: Invisible Retainers, *Orthodontic and Orthopedic Treatment in the Mixed Dentition*, Needham Press, Jan. 1993. pp. 347-353.

Moermann et al., "Computer Machined Adhesive Porcelain Inlays: Margin Adaptation after Fatigue Stress," IADR Abstract 339, *Journal of Dental Research*, vol. 66(a) (1987), p. 763.

Mörmann et al., "Marginal Adaptation von adhasiven Porzellaninlays in vitro," *Schwizerische Monatsshrift fur Zahnmedizin*, vol. 85 (1985), p. 1118-1129.

Nahoum, "The Vacuum Formed Dental Contour Appliance" *The New York State Dental Journal*, 30(9):385-390, Nov. 1964.

Nash, "CEREC CAD/CAM Inlays: Aesthetics and Durability in a Single Appointment," *Dentistry Today*, (Oct. 1990), pp. 20, 22-23, 54.

Nishiyama et al., "A New Construction Of Tooth Repositioner By LTV Vinyl Silicone Rubber" J. Nihon University School of Dentistry, 19(2):93-102, 1977.

Pinkham, "Foolish' Concept Propels Technology," *Dentist*, Jan./Feb. 1989, 3 pages total.

Pinkham, "Inventor's CAD/CAM May Transform Dentistry," *Dentist*, Sep. 1990, 3 pages total.

Ponitz, "Invisible Retainers", *Am. J. Orthodontics*, vol. 59, No. 3, Mar. 1971, pp. 266-272.

Procera Research Projects, *PROCERA Research Projects 1993—Abstract Collection*, 1993, pp. 3-24.

Rekow, "A Review of the Developments in Dental CAD/CAM Systems,"(contains references to Japanese efforts and content of the papers of particular interest to the clinician are indicated with a one-line summary of their content in the bibliography), Dental Clinics: *Prosthodontics and Endodontics*, pp. 25-33, 1992.

Rekow "CAD/CAM in Dentistry: A Historical Perspective and View of the Future," *Journal*, vol. 58 No. 4, Apr. 1992), pp. 283, 287-288.

Rekow, "Computer-Aided Design and Manufacturing in Dentistry: A Review of the State of the Art," *The Journal of Prosthetic Dentistry*, vol. 58, No. 4 (Oct. 1987), pp. 512-516.

Rekow, "Dental CAD-CAM Systems: What is the State of the Art?" *Journal of the American Dental Assoc.*, vol. 122 (1991), pp. 43-48.

Rekow, "Feasibility of an Automated System for Production of Dental Restorations," PHD Thesis Univ. of Minnesota, Nov. 1988, 244 pages total.

Richmond et al., Research Reports, "The Development of a 3D Cast Analysis System," *British Journal of Orthodontics*, vol. 13, No. 1 (Jan. 1986) pp. 53-54.

Richmond "Recording the Dental Cast in Three Dimensions," *Am. J. Orthod. Dentofac. Orthop.*, vol. 92, No. 3, (Sep. 1987), pp. 199-206.

Rudge, "Dental arch analysis: Arch Form, A review of the literature," *European Journal of Orthodontics*, vol. 3, No. 4 (1981), pp. 279-284.

Sakuda et al., "Integrated information-processing system in clinical orthodontics: An approach with use of a computer network system," *Am. J. Orthod. Dentofac. Orthop.* vol. 101 No. 3 (Mar. 1992), pp. 210-220.

Schellhas et al., "Three-Dimensional Computed Tomography in Maxillofacial Surgical Planning," *Arch Otolamgol Head Neck Surg.* vol. 114 (Apr. 1988), pp. 438-442.

Shilliday, "Minimizing Finishing Problems With the Mini-Positioner" *Am. J. Orthod.* 59:596-599, 1971.

Siemens, "CEREC—Computer-Reconstruction," High Tech in der Zahnmedizin, 14 page total.

Sirona Dental Systems GmbH, CEREC 3D, Manuel utilisateur, Version 2.0X (in French), 2003, 114 pages total.

Stoll et al., "Computer-aided Technologies in Detistry" (Article Summary in English, article in German), Dtsch Zahnä rztl Z 45, 314-322, 1990.

U.S. Department of Commererce, National Technical Information Service, "Automated Crown Replication Using Solid Photography SM,"Solid Photography Inc. Melville NY, Oct. 1977, 20 pages total.

U.S. Department of Commerce, National Technical Information Service, "Holodontography: An Introduction to Dental Laser Holography," School of Aerospace Medicine Brooks AFB Tex, Mar. 1973, 37 pages total.

U.S. Appl. No. 60/050,342, filed Jun. 20, 1997, 41 pages total.

Van Der Linden et al., "Three-Dimensional Analysis of Dental Casts by Means of the Optocom," *J Dent Res*, Jul.-Aug. 1972, vol. 51, No. 4, p. 1101.

Van Der Linden, "A New Method to Determine Tooth Positions and Dental Arch Dimensions," Jul.-Aug. 1972, p. 1104.

Van Der Zel, "Ceramic-fused-to-metal Restorations with a New CAD/CAM System," *Quintessence International*, vol. 24(11) (1993), pp. 769-778.

Várady et al., Reverse Engineering of Geometric Models—An Introduction. Computer-Aided Design, 29 (4):255-268, 1997.

Warunek et al., "Clinical Use of Silicone Elastomer Appliances" *JCO*, MH (10:694-700, 1989.

Warunek et al., "Physical And Mechanical Properties of Elastomers in Orthodontic Positioners" *Am. J. Orthod. Dentofac. Orthop.*, 95:388-400, 1989.

Wells, "Application of the Positioner Appliance in Orthodontic Treatment" *Am. J. Orthodont.*, 58:351-366, 1970.

Williams, "Dentistry and CAD/CAM: Another French Revolution," *Journal of Dental Practice Admin.*, Jan./Mar. 1987, pp. 2-5.

Williams, "The Switzerland and Minnesota Developments in CAD/CAM," *Journal of Dental Practice Admin.*, pp. 50-55, Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990, AAOMS 72nd Annual Meeting and Scientific Sessions, Sep. 13, 1990, New Orleans, *Journal of Oral and Maxillofacial Surgery*, vol. 48, No. 8, Supp. Aug. 1, 1990, p. 5.

Yamamoto et al., "Three-Dimensional Measurement of Dental Cast Profiles and Its Applications to Orthodontics," Annual Int'l Conf. of IEEE Engineering in Medicine and Biology Society, vol. 12, No. 5, pp. 2051-2053, 1990.

Yamamoto et al., "Optical Measurement of Dental Cast Profile and Application to Analysis of Three-Dimensional Tooth Movement in Orthodontics," *Frontiers in Med. and Biol. Eng'g*, vol. 1, No. 2 (1988), pp. 119-130.

\* cited by examiner

DENTAL TRAY CONTAINING RADIOPAQUE MATERIALS

BACKGROUND

The present invention relates generally to dental impression trays.

In dental applications, an impression is often used to create an imprint or negative likeness of the teeth and adjacent portions of the jaw (e.g., tooth formations, the contour of the gums, etc.) preparatory to dental repair, orthodontics and restoration of missing dental structures. Impressions are typically made by placing a soft, semi-fluid material within the confines of an open trough or channel of an arcuate tray which is then positioned within the mouth of a patient, thus allowing the material to set or cure. Depending upon the material used, the set impression may be either hard or have some elastic characteristics.

To provide the most accurate articulation, the impression cast should generally represent the entire dental arch. In this regard, the impression cast can be used to establish interproximal contacts, buccal and lingual contours and occlusion with the opposing teeth. From the negative or female cast of the teeth and surrounding structures, a positive reproduction or male cast may be created for the purpose of fabricating inlays, crowns, bridge retainers, dentures, restorations or the like.

Traditionally, before an impression cast of the dentition is created, a stock tray is selected by the dentist or dental assistant that will generally fit the dental arch of the particular patient. Since the dental arch may differ widely from patient to patient, various sizes of impression trays (e.g., small, medium and large) were developed by those skilled in the art to accommodate various mouth sizes, bite radii of teeth and to correspond to upper and lower anterior or quadrant impression sites.

As described in U.S. Pat. No. 6,629,841, certain dental impression trays formed of metal, such as stainless steel, have a pair of spaced-apart vertical walls joined by a semi-rigid mat or mesh material disposed horizontally between the opposing vertical walls. Extending outwardly in structural relation to at least a portion of the surface facing of one of the vertical walls, a handle member may be provided to facilitate a means for gripping the impression tray for purposes of manual manipulation. In addition, an open trough or channel is generally formed between the opposing vertical walls, wherein the horizontally disposed mesh material provides porous surface flooring for the trough. In operation, the mesh material provides a means for permitting excess flow of impression material to become displaced and extruded there through. Dental impression trays of the prior art may further include openings formed in the vertical walls of the trough or channel which generally function as an anchoring surface for the impression, thus allowing the excess flow of impression material to become attached thereto.

SUMMARY

In one aspect, a method to create a digital model of a patient's teeth includes taking an impression of the patient's teeth using a dental tray containing a radiopaque material; scanning the impression and the dental tray using a radiographic source; and generating the digital model with scanned data.

In another aspect, a dental impression system includes a dental tray containing a radiopaque material adapted to receive a dental impression material thereon. The tray includes a base having a plurality of prongs, the base having one or more openings to allow flowing of the dental impression material; a wall extending from one side of the base, the wall having one or more openings to allow flowing of the dental impression material. A container houses the radiographic tray, both of which are then adapted to be scanned by a radiographic scanner.

In yet another aspect, a system to create a digital model of a patient's teeth includes a dental tray containing a radiopaque material adapted to take an impression of the patient's teeth; a radiation source; a scintillator to receive the radiation from the radiation source; a radiation detector coupled to the scintillator; a rotatable table positioned between the radiation source and the scintillator, the table being adapted to support the dental tray with the impression of the patient's teeth; and a computer coupled to the detector to generate the digital model with scanned data.

Advantages of the system may include one or more of the following. The dental tray's detachable portions allow the trays to be customized to the patient's particular physiology. The dental tray's detachable portions can be snapped off during use to accommodate various mouth sizes, bite radii of teeth, and to correspond to upper, lower, anterior, quadrant, or triple bite impression sites. The adjustable dental impression tray is formed of a disposable material, thus avoiding the disadvantages associated with having to clean and sanitize metal impression trays. The adjustable dental impression tray may be adjusted to the specific size of the patient's mouth, thereby eliminating the need for a dentist to stock various sizes of impression trays (e.g., small, medium, and large) in order to accommodate different dental arch configurations. The adjustable dental impression tray increases the accuracy of the impression cast, while decreasing dental chair time. The adjustable dental impression tray reduces the possibility of deformation of the impression cast. The adjustable dental impression tray is simple in construction, effective in operation, and inexpensive to manufacture.

Other features, objects and advantages of the present invention will become apparent from a reading of the following description as well as a study of the appended drawings.

BRIEF DESCRIPTION OF THE DRAWINGS

A dental impression tray incorporating the features of the invention is depicted in the attached drawings which form a portion of the disclosure and wherein.

DESCRIPTION

Figure 1:
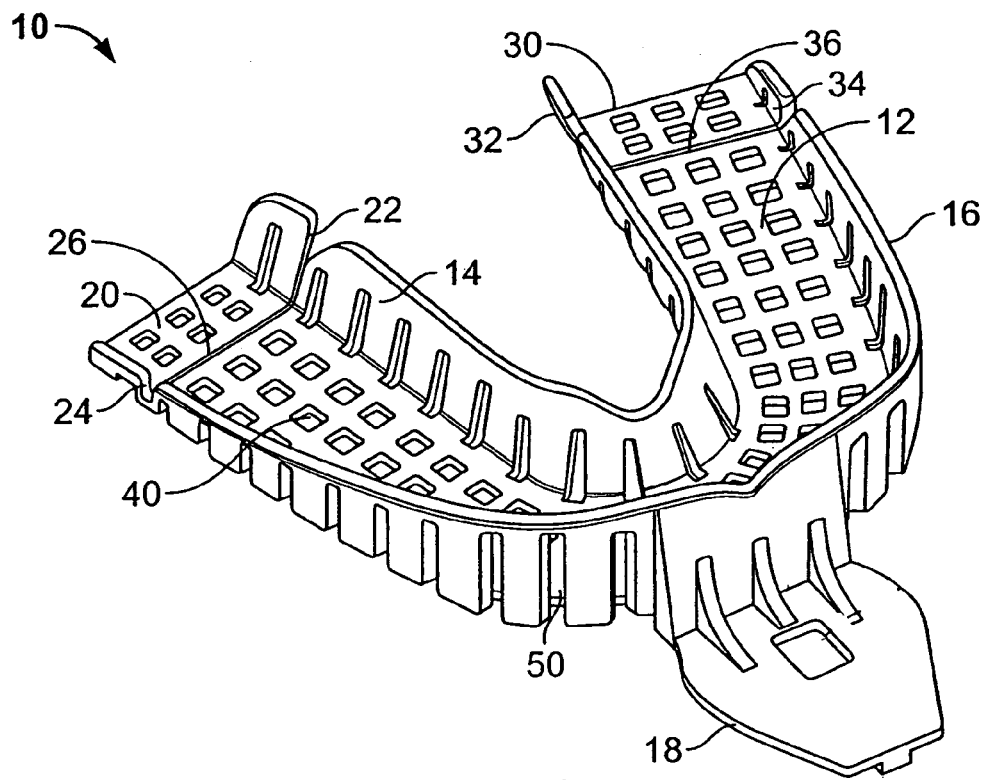
FIG. 1 is a perspective view of a dental impression tray utilized to take dental impressions.
Figure 2:
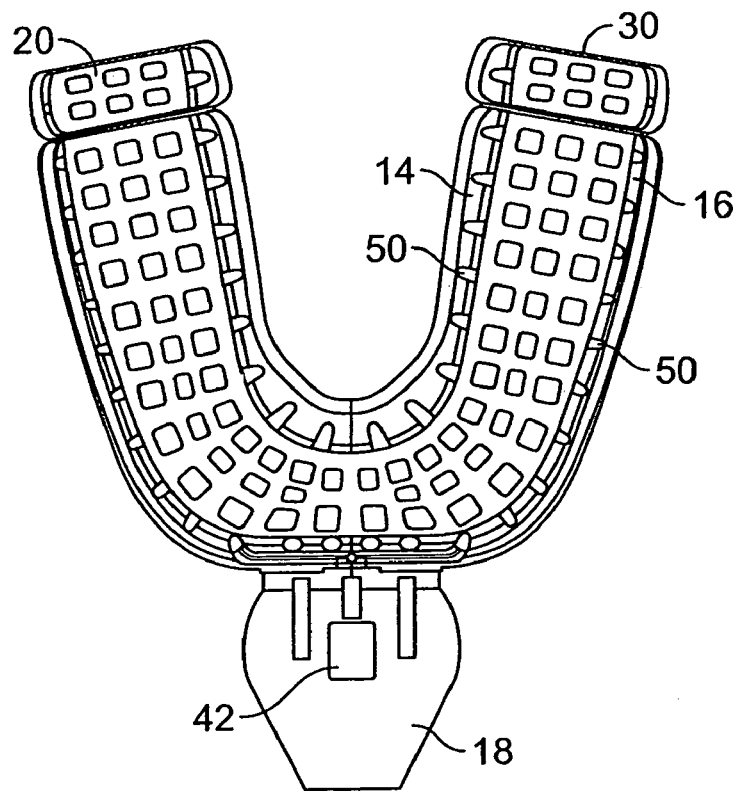
FIG. 2 shows a top view of the tray of FIG. 1.
Figure 3:
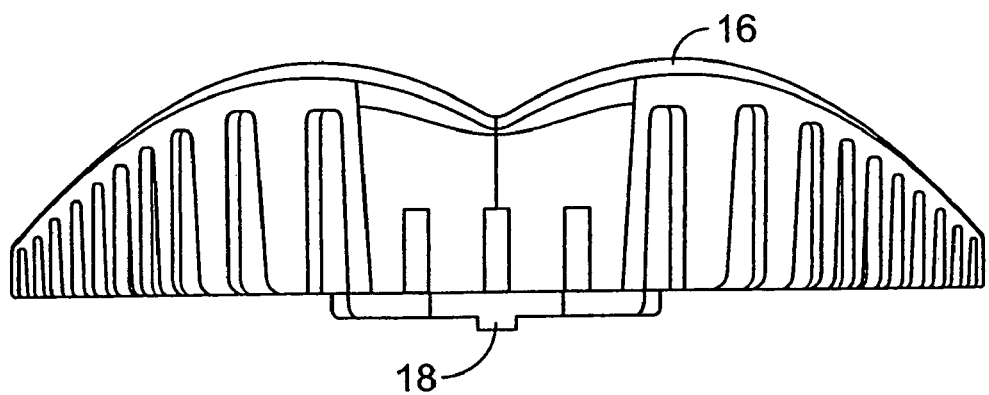
FIG. 3 shows a front view of the tray of FIG. 1.
Figure 4:
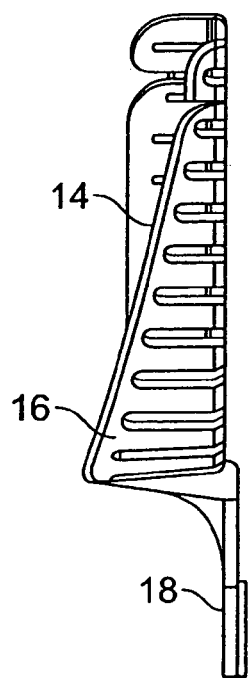
FIG. 4 shows a side view of the tray of FIG. 1.

FIG. 1 is a perspective view of a dental impression tray utilized to take dental impressions. The dental tray is designated by reference number 10. FIG. 2 shows a top view of the tray 10, while FIG. 3 shows a front view of the tray 10 and FIG. 4 shows a side view of the tray 10.

The dental impression tray 10 is typically fabricated from either a thermoplastic resin or metal and includes a tray base 12, an inner tray wall 14 and an outer tray wall 16, each of which may have the same thickness, different thicknesses, or varying wall thicknesses. The inner wall 14 defines a tray recess for accommodating an individual's tongue when taking an impression, while the outer and inner tray walls 14-16 define a receiving region to receive an impression material. The tray 10 includes a tab or a handle 18 to facilitate handling by a user such as a dental professional. The base 12 and the handle 18 include one or more openings 40 which allow impression materials to flow from the receiving region as the tray is pressed against a patient's teeth. Additionally, one or more openings 50 can be formed on the walls 14-16 to allow impression materials to flow from the receiving region as well. The openings 40 and 50 may take a variety of shapes. As illustrated, the openings 40 are square, but may be rectangular or oval or rectilinear in shape. Also, the openings 50 can be triangular, semi-spherical, or semi-oval in shape.

Figure 1A:
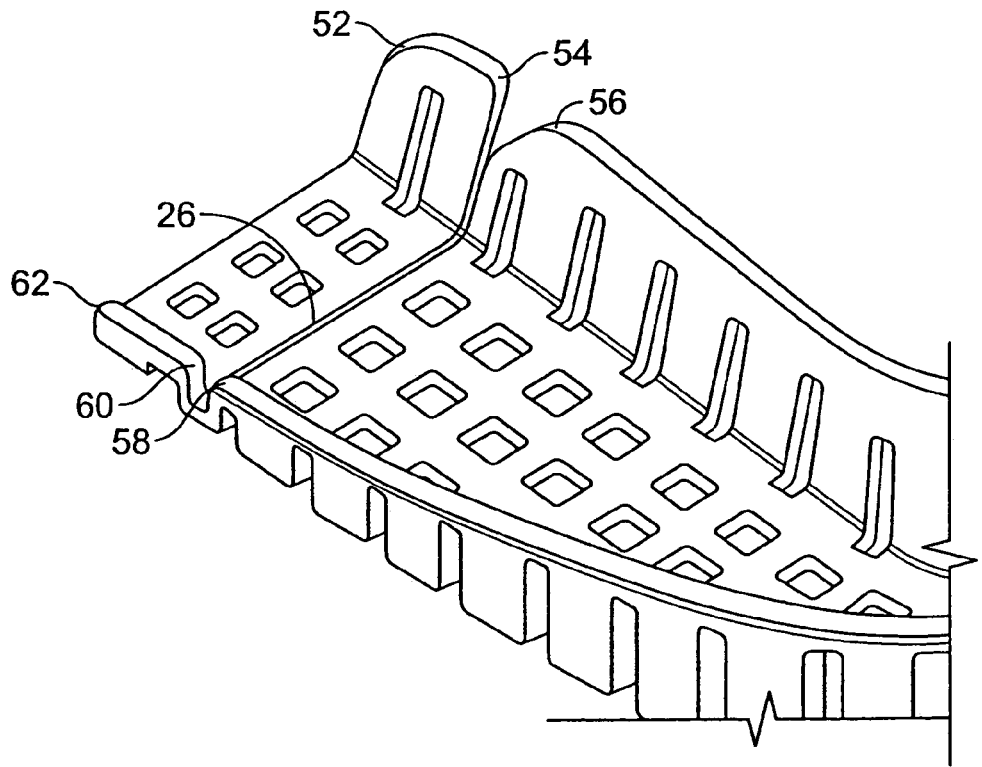
FIG. 1A is an enlarged view of a portion of the tray of FIG. 1.

The dental impression tray 10 also includes one or more detachable portions 20 and/or 30. Notches define one detachable portion from another. For example, notches 22 and 24 separate the portion 20 from the rest of the tray 10, while notches 32 and 34 separate the portion 30 from the tray 10. A score or a ridge 26 runs between notches 22-24, and correspondingly a ridge 36 runs between notches 32 and 34. The ridge 26 provides a structurally weakened region that allows the detachable portion 20 to be cleanly snapped off the tray 10 to shorten the tray 10 to accommodate patient physiology. Similarly, the ridge 36 allows the user to snap off the detachable portion 30 to adjust the tray 10 to accommodate the patient's jaw. In one implementation, the ridge has a depth that is about half of the thickness of the wall 14 or 16. FIG. 1A shows in more detail the portion 20. In FIG. 1A curved corners 52, 54, 56, 58, 60 and 62 of the vertical walls near ridge 26 are rounded in shape with a radius of from about 3 to 7 mm. Similarly, the inner and outer edges of these corners are proximally rounded. The rounded corners and edges significantly reduce patient discomfort when the tray comes in contact with the delicate oral tissues. FIG. 2 shows a top view of the tray 10, while FIG. 3 shows a front view of the tray 10 and FIG. 4 shows a side view of the tray 10.

While FIGS. 1-4 show an embodiment adapted to take a lower impression of the patient's dentition, FIGS. 5-8 show another embodiment adapted to take an upper impression of the patient's dentition.

Figure 5:
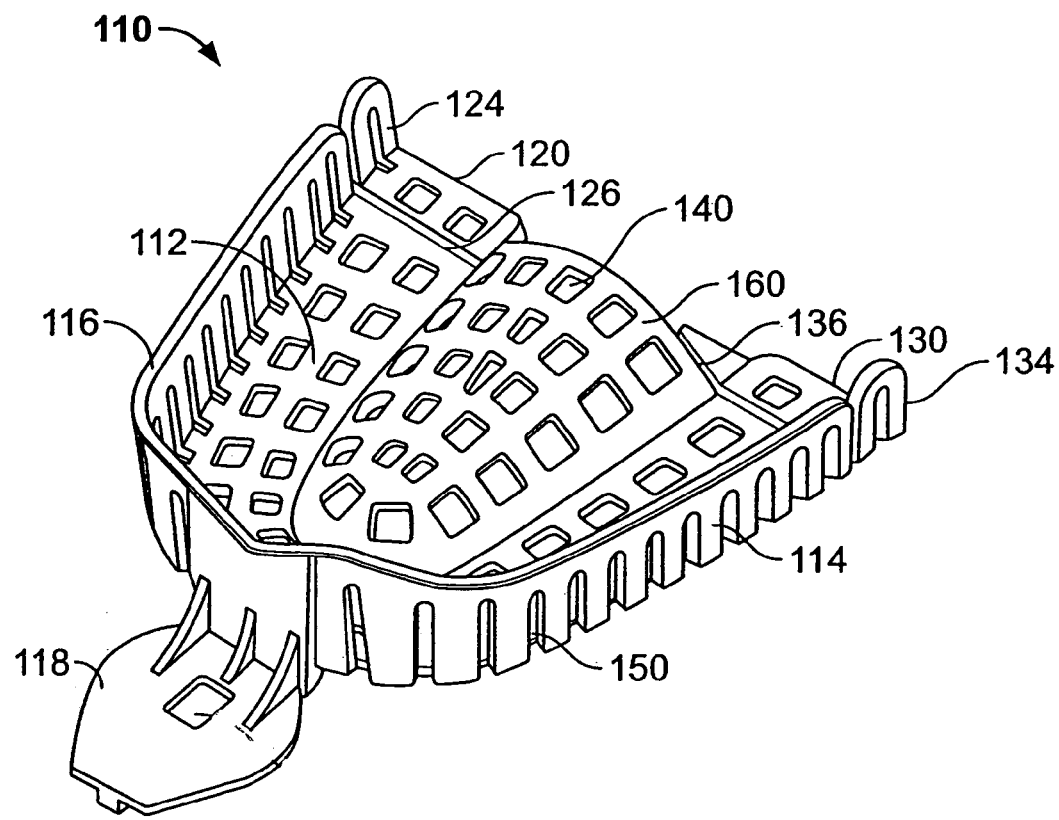
FIG. 5 is a perspective view of a second embodiment dental impression tray utilized to take dental impressions.

FIG. 5 is a perspective view of a second embodiment dental impression tray 110 utilized to take dental impressions. In place of an inner wall, the tray 110 has a curved surface or portion 160 connecting the interior portion of a base 112. Similar to the dental impression tray 10, the tray 110 includes a tray base where the arcuate portion 160 interconnects the inner edges of the tray base and an outer tray wall. The parts of the tray 110 may have the same thickness, different thicknesses, or varying thicknesses. The tray 110 includes a tab or a handle 118 to facilitate handling by a user such as a dental professional. The base 112 includes one or more openings 140 which allow impression materials to flow from the receiving region as the tray is pressed against a patient's teeth. Additionally, one or more openings 150 can be formed on the walls 114-116 to allow impression materials to flow from the receiving region as well. The openings 140 and 150 may take a variety of shapes. As illustrated, the openings 140 are square, but may be rectangular or oval or rectilinear in shape. Also, the openings 150 can be triangular, semi-spherical, or semi-oval in shape.

The dental impression tray 110 also includes one or more detachable portions 120 and/or 130. A ridge 126 runs between notch 124 and the arcuate portion 160, and correspondingly a ridge 136 runs between notch 134 and arcuate portion 160. The ridge 126 provides a structurally weakened region that allows the detachable portion 120 to be cleanly snapped off the tray 110 to shorten the tray 110 to accommodate patient physiology. Similarly, the ridge 136 allows the user to snap off the detachable portion 130 to adjust the tray 110 to accommodate the patient's upper jaw.

Figure 6:
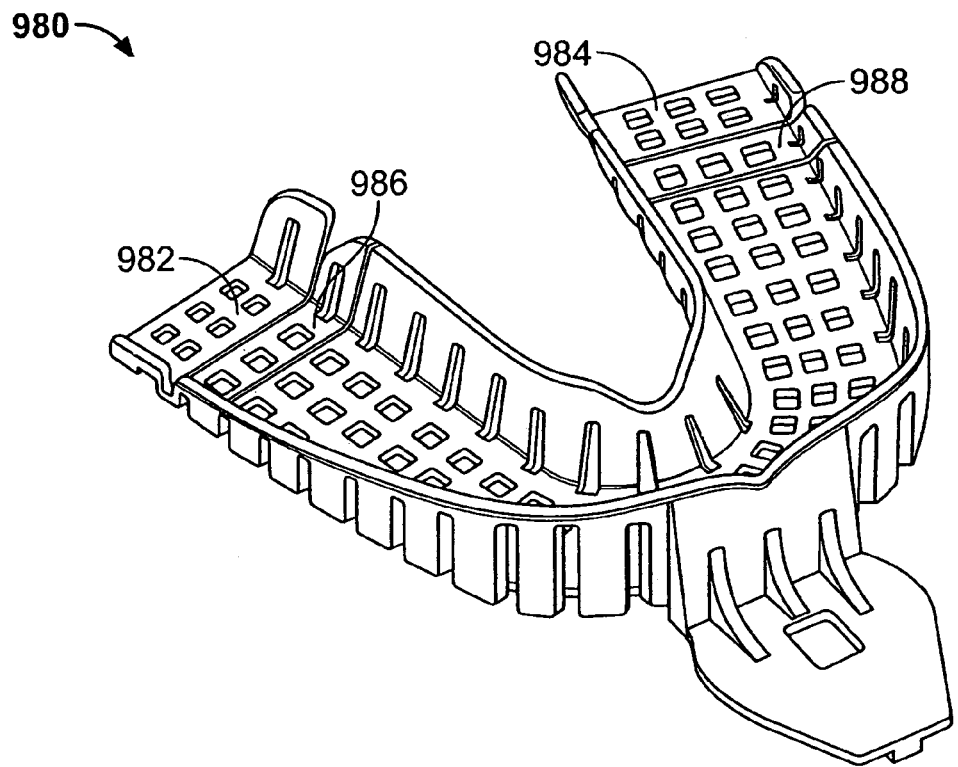
FIGS. 6-7 show perspective and top views of another tray embodiment.
Figure 7:
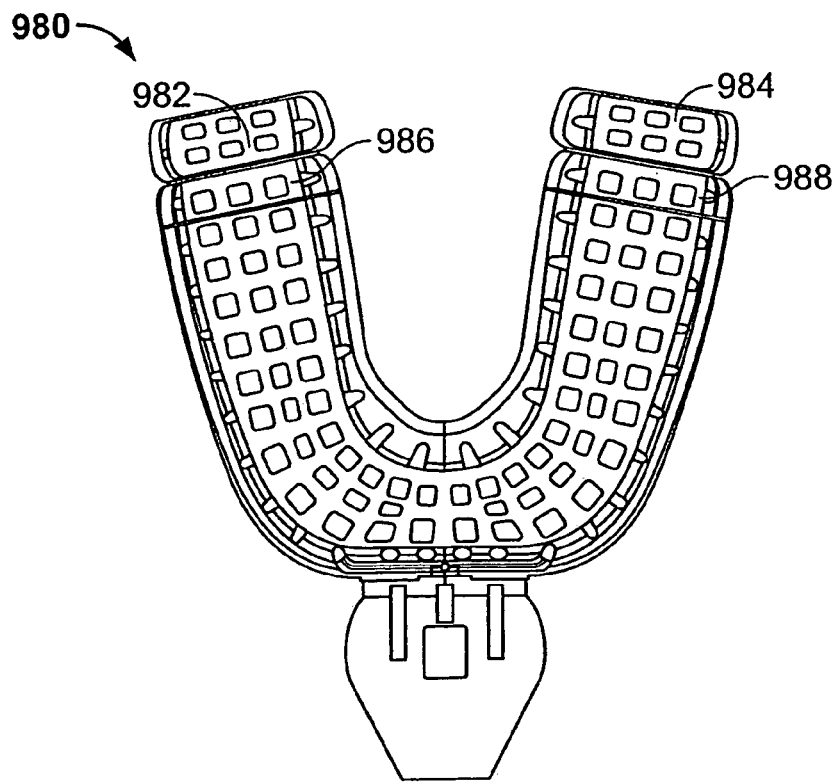

FIG. 6 shows a perspective view of another embodiment, while FIG. 7 shows a top view of the embodiment of FIG. 6. As shown therein, an exemplary dental impression tray 980 with a plurality of detachable portions 982, 984, 986 and 988, among others. In this embodiment, a user can remove one or more of the detachable portions 982-988 as desired to better conform the dental impression tray 980 to a patient's anatomy. In the embodiment of FIG. 6, the detachable portions 982-988 are removed in sequence that is the end portion must be removed before the next portion can be removed. To illustrate, the portion 982 should be removed so expose the portion 986 for removal. Similarly, the portion 984 should be removed to allow the user access to the portion 988.

Figure 8:
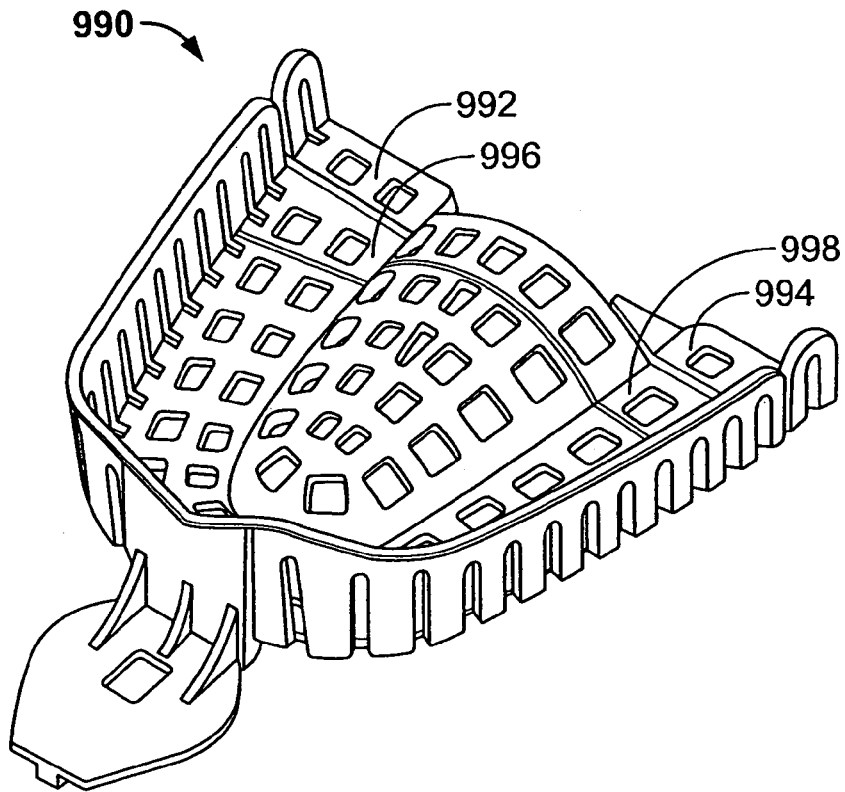
FIGS. 8-9 show perspective and top views of yet another tray embodiment.
Figure 9:
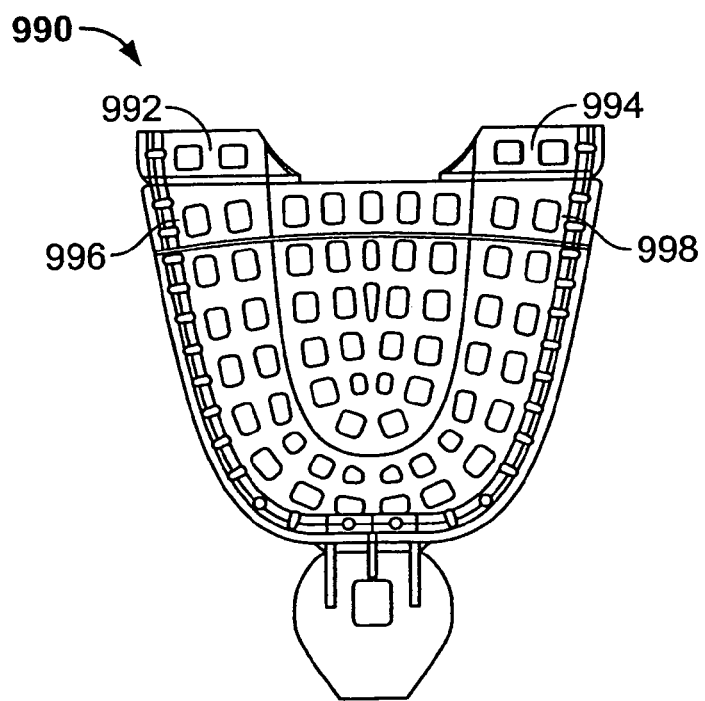

FIG. 8 shows a perspective view of yet another embodiment, while FIG. 9 shows a top view of the embodiment of FIG. 8. As shown in FIG. 8, an exemplary dental impression tray 990 with a plurality of detachable portions 992, 994, 996 and 998, among others. In this embodiment, a user can remove one or more of the detachable portions 992-998 as desired to better conform the dental impression tray 990 to a patient's anatomy. In the embodiment of FIG. 8, the detachable portions 992-998 are removed in sequence that is the end portion must be removed before the next portion can be removed. To illustrate, the portion 992 should be removed so expose the portion 996 for removal. Similarly, the portion 994 should be removed to allow the user access to the portion 998.

A variety of thermoplastics may be used to manufacture an acceptable dental impression tray. The nature of the dental tray resin is not particularly critical as long as it is of a suitable medical grade quality, provides sufficient rigidity when injection molded and is compatible with the x-ray attenuating agent. Suitable thermoplastic resins include but are not limited to polyurethane, polyester, polycarbonate, ABS and polystyrene.

In one implementation, a radiopaque agent is added to the thermoplastic resins to attenuate the intensity of a scanner's X-ray beam and to improve the quality of the scan data. An example of a thermoplastic polyurethane resin that may be compounded with a radiopaque agent and may be injection molded to produce dental impression trays is Tecoplast, for example OP 800 B03 BL 294.

The radiopacity of the thermoplastic impression tray depends on its atomic number and density which may be controlled by compounding a radiopaque agent(s) into the thermoplastic resin. Suitable radiopaque agents include barium sulfate, calcium carbonate, calcium chloride, sodium carbonate, magnesium sulfate, bismuth trioxide, bismuth subcarbonate, bismuth oxychloride and the heavy metal powder tungsten, gold, platinum, silver. The type and amount of radiopacifier depends on the thermoplastic resin, the impression tray wall thickness, the type of impression material used to take the dental impression as well as the X-ray source and detector. For the computed tomography scanning method employed it is recommended that the X-ray characteristics of the dental tray be formulated so that its radiopacity matches or closely approximates the radiopacity of the impression material. In general the attenuation factor of the impression tray should not exceed the attenuation factor for the impression material by more than 50%. For example, the x-ray attenuation factor for a typical commercially available polyvinylsiloxane impression material is about 1.7 when compared to a water standard which is 1.0. A dental impression tray fabricated from a medical grade polyurethane thermoplastic resin without any radiopaques additives has a X-ray attenuation factor of about 0.4-0.5. This value is too low and will not allow for optimum resolution of the two materials and consequently the computer algorithm will not properly reconstruct the dental impression image. In contrast, a polyurethane resin or polycarbonate resin formulated with 3%+/−1% of the radiopaque agent barium sulfate or 25%+/−3% calcium carbonate has a X-ray attenuation factor of 1.4 relative to the water standard 1.0. This attenuation factor is close to the attenuation factor for the PVS resin and allows for accurate reconstruction of the dental image.

The impression tray 10 or 110 and impression material are then introduced into a patient's mouth. An impression is made by the dentist positioning the impression tray and impression material over the patient's teeth and applying pressure so that the impression material disperses around the teeth and dental arch while the dental impression material is curing. To obtain an accurate impression, the impression material must be pushed against the teeth and gums, so that there are no gaps between the teeth and gums and the impression material. To capture the patient's upper arch, the tray is inserted with the base 12 facing down. To capture the patient's lower arch, the tray is inverted so that the tray base 12 is disposed upwardly. It will be appreciated that the tray interior accommodates a teeth impression material such as wax. After the impression has been made by virtue of the dentist pressing the patient's teeth into the impression material, the tray and impression material are removed from the mouth after the impression material have cured and will not flow or deform. Excess impression material may be trimmed from the lingual recess of the dental impression tray.

A wide range of impression materials is available for taking dental impressions. The major chemical classes of elastomeric impression materials include irreversible hydrocolloids, reversible hydrocolloids, polysulfide, polyether, condensation reaction silicones and addition reaction silicones. Of these, irreversible hydrocolloids, addition reaction silicones and polyethers are the most popular materials used by professionals for taking dental impressions. Alginates are examples of irreversible hydrocolloids formed by combining the sodium salt of alginic acid, calcium sulfate and water. Commercially available alginate impression materials include Jeltrate® (Dentsply/Caulk), Coe Alginate® (Coe) and Kromopan® (Lascod S.p.A.). Polyethers come as a two part system consisting of base and catalyst pastes. The base contains a polyether with imine end groups and the catalyst contains an aromatic sulfonic acid. These components may be either mixed by hand or dispensed from a dual chambered cartridge that automatically mixes the correct proportions of base and catalyst material. Commercially available polyether materials include Impregum F® (ESPE), Permadyne® (ESPE) and Polyjel® (Dentsply/Caulk). Like polyethers, addition reaction silicones are a two part system consisting of base and catalyst pastes. These materials are also called polyvinylsiloxanes (abbreviated PVS) or vinyl siloxanes since vinyl groups are present as terminal end groups in one paste. The other paste contains terminal hydrogens. When mixed together they form a highly cross-linked elastomeric material which recovers well from deformation. Commercially available PVS impression materials include Splash® (Discus Dental), Aquasil® (Dentsply/Caulk) and Dimension® (ESPE).

Depending on the radiopacity of the tray and impression materials in some applications it may be useful to directly compound a radiopaque material into the impression material to achieve a desired attenuation. The radiopaque material may be formulated into the impression materials described previously. For example, for powdered alginate materials the radiopaque compound could be dry blended into the component mixture. For polyethers and polyvinylsiloxanes that come as a two part system the radiopaque material would be mixed and dispersed with either the base or catalyst pastes. An impression material formulated with a radiopaque material may be used to capture full arch, dual arch, single arch, partial arch impressions or bite relationship impressions. Furthermore, in addition to being premixed into the impression material, the radiopaque material may be in the form of a spray, dip, or powder layer that is used to coat the surface of the impression material in order to make the surface more visible to the scanner after the impression has been captured, but prior to the scan.

Figure 10:
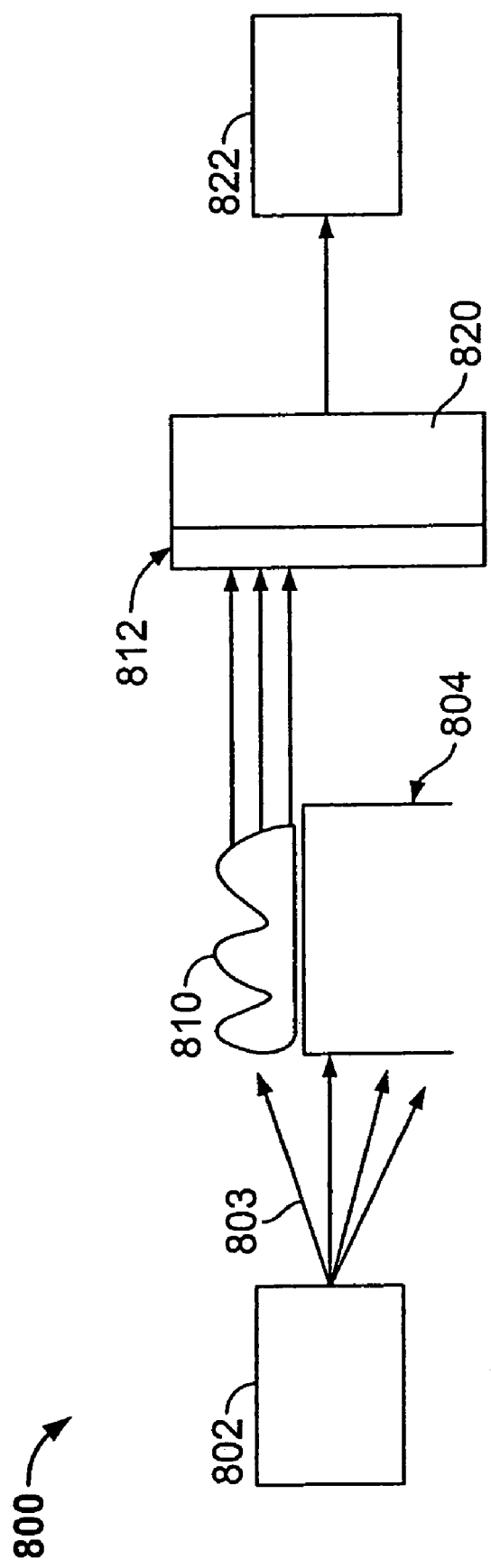
FIG. 10 shows an exemplary radiographic scanning system.

The tray and the impression material are eventually provided to a scanner to obtain 3-D dental information for the patient. FIG. 10 shows one embodiment of the scanner, which in this embodiment is an X-ray scanner. The scanner 800 has a rotating table 804 including a table top that has sufficient space for one or two impressions 810 to rest on it. The impression 810 can be irradiated by a flat fan-shaped X-ray beam 803 emitted by an X-ray source 802. The radiation is swept by the impression 810 and passes through a scintillator 812. Radiation transmitted by the scintillator 812 is measured by an X-ray detector 820. The detector 820 performs an analog to digital conversion and provides this information to a computer 822. The computer 822 captures on cross sectional scan and instructs the rotating table 804 to rotate to its next position and another scan is performed until the entire impression 810 is scanned. The X-ray source 802, the scintillator 812, the detector 820 and the rotatable table 804 thus obtains an image of a cross-section of (a part of) the impression 810 by computer tomography (CT). The CT system scans impressions of patients' teeth and eliminates the need to create a plaster model for each jaw. Software on the computer 822 automatically extracts a positive model out of the scan data. The upper and lower jaw will then be put together using the information from the scan data of a wax bite. In one embodiment, the scanner 800 utilizes a technique called "cone beam reconstruction."

Figure 11:
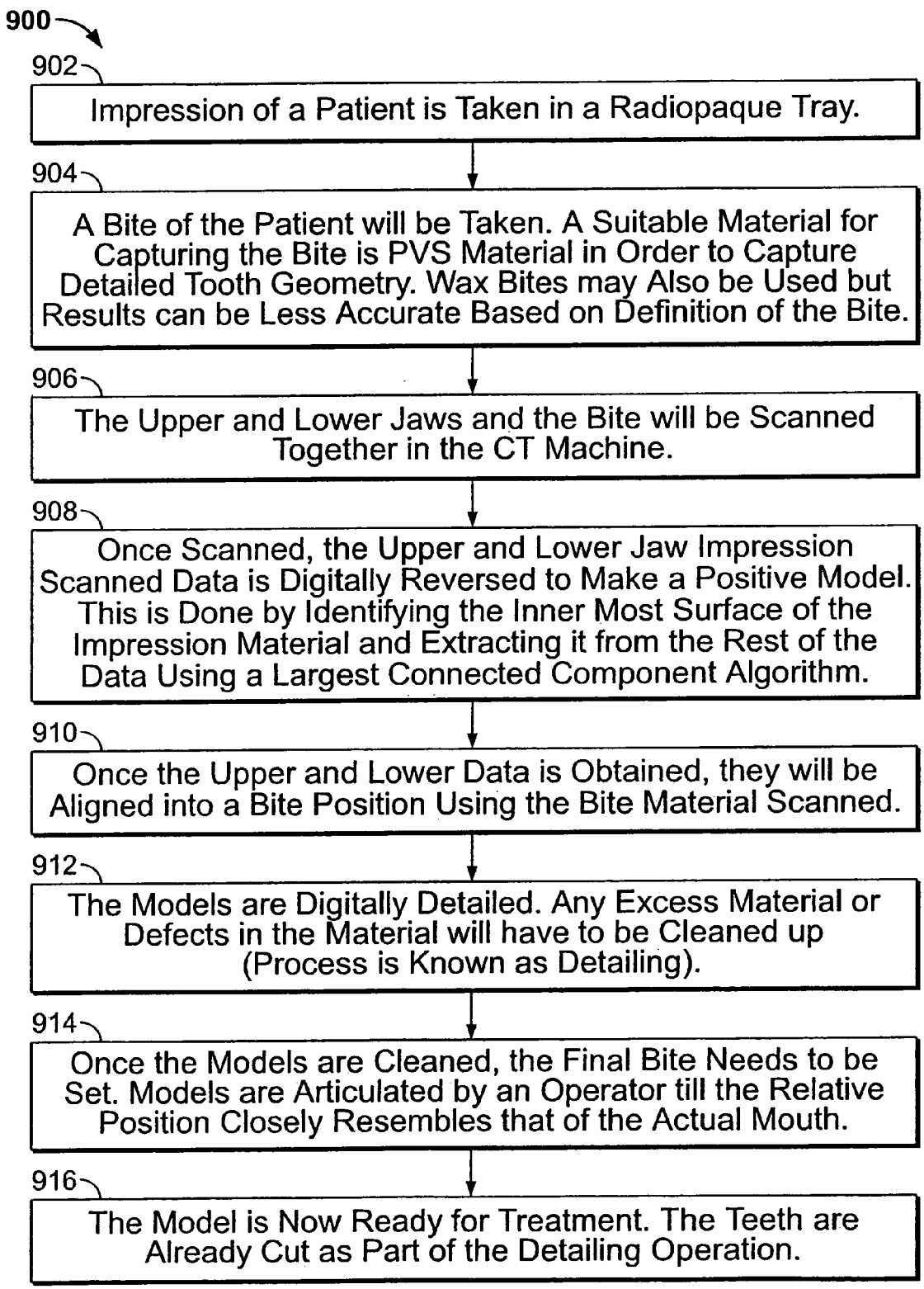
FIG. 11 shows an exemplary process for generating a digital model of a patient's teeth using the trays.

FIG. 11 shows one process 900 for digitally scanning and generating a model of the patient's teeth for treatment. The process 900 is as follows:

1. Impression of a patient is taken in a radiopaque tray (902).
2. A bite of the patient will be taken. A suitable material for capturing the bite is PVS material in order to capture detailed tooth geometry. Wax bites may also be used but results can be worse based on definition on the bite (904).
3. The upper, lower and the bite will be scanned together in the CT machine (906).
4. Once scanned, the upper and lower impression scanned data is digitally reversed to make a positive. This is done by identifying the inner most surface of the impression material and extracting it from the rest of the data using a largest connected component algorithm (908).
5. Once the upper and lower data is obtained, they will be aligned into a bite position using the bite material scanned (910).
6. The models are digitally detailed. Any excess material or defects in the material will have to be cleaned up (process is known as detailing) (912).
7. Once the models are cleaned, the final bite needs to be set. Models are articulated by an operator till the relative position closely resembles that of the actual mouth (914).
8. The model is now ready for treatment. The teeth are already cut as part of the detailing operation (916).

In one aspect, a method creates a digital model of a patient's teeth by creating a radiographic impression of the patient's teeth; scanning the impression using an X-ray source; and generating the digital model with scanned data. Implementations of the above aspect may include one or more of the following. The radiation source may be passed through a scintillator. The output of the scintillator is then digitized. The impression of the teeth can be taken in a dental tray. A bite impression of the patient can also be taken. The bite impression is taken using a PVS material or a wax bite. The upper teeth impression, a lower teeth impression and a bite impression can be scanned together. The data for the upper and lower impression scan data to make positive data can be digitally reversed. The digital reversing identifies inner surfaces of an impression material and extracting the inner surfaces using a largest connected component algorithm. The data can be aligned into a bite position using the bite material scanned. The digitized teeth data can be digitally detailed. A final bite can be determined. The digital model can be virtually articulated. A computer representation of a masticatory system of the patient can be generated and the computer can determine an occlusion from the computer representation of the masticatory system. The system can register a model of the upper and lower teeth with a model of the masticatory system; simulate the motion of the jaws to generate contact data between the upper and lower teeth; and place teeth in a final position based on the contact data. The system can apply kinematics to the model of the teeth. A constrained motion can be applied to the model of the tooth. The position of the tooth can be determined according to a measure of undesirability. The measure of undesirability is a function of one or more of Peer Assessment Rating (PAR) metrics, distance-based metrics and shape-based metrics. A library of motions can be applied to the digital model of the teeth. The library of motions includes protrusive motion, lateral motion, and tooth-guided motion. Physical forces can be applied to the teeth model.

In another aspect, an apparatus to create a digital model of a patient's teeth includes a radiation source; a scintillator to receive the radiation from the radiation source; a radiation detector coupled to the scintillator; a rotatable table positioned between the radiation source and the scintillator, the table being adapted to support an impression of the patient's teeth; and a computer coupled to the detector to generate the digital model with scanned data. A fabrication machine can be driven by the computer to generate a plurality of appliances, wherein the appliances comprise polymeric shells having cavities and wherein the cavities of successive shells have different geometries shaped to receive and resiliently reposition the teeth from one arrangement to a successive arrangement. Such systems are described in U.S. Pat. Nos. 6,633,789; 6,629,840; 6,626,666; 6,621,491; 6,607,382; 6,602,070; 6,582,229; 6,582,227; 6,572,372; 6,554,611; 6,524,101; 6,514,074; 6,499,997; 6,497,574; 6,488,499; 6,485,298; 6,471,511; 6,463,344; 6,457,972; 6,454,565; 6,450,807; 6,409,504; 6,406,292; 6,398,548; 6,394,801; 6,390,812; 6,386,878; 6,386,864; 6,371,761; 6,318,994; 6,309,215; 6,299,440; 6,227,851; 6,227,850; 6,217,325; 6,210,162; 5,975,893, the contents of which are hereby incorporated by reference.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

The ridges can also be creases or lines of perforations running horizontally, vertically, or angled through the tray. Alternatives to the ridges to allow the detachable portions to be removed such as flanges are within the scope of the invention.

While the invention has been shown and described with reference to an embodiment thereof, those skilled in the art will understand that the above and other changes in form and detail may be made without departing from the spirit and scope of the following claims.

What is claimed is:

1. A method of creating a digital model of a patient's teeth, comprising:
    taking an impression of the patient's teeth using a dental impression system configured to improve the quality of scanned data from a dental impression, the system including an impression material and a dental tray adapted to hold the impression material, the dental tray made of a tray material, each of the impression and tray material having a respective radiopacity, at least one of the materials being formulated with a radiopaque agent such that the respective radiopacities of the materials approximately match each other;

scanning the impression and the dental tray using a radiographic source; and generating the digital model with scanned data.

2. The method of claim 1, further comprising passing a radiation source through a scintillator.

3. The method of claim 2, further comprising digitizing the output of the scintillator.

4. The method of claim 1, wherein the impression of the teeth is taken in a dental tray having detachable portions.

5. The method of claim 1, further comprising taking a bite impression of the patient.

6. The method of claim 5, wherein the bite impression is taken using a PVS material.

7. The method of claim 5, wherein the bite impression is taken using a wax bite.

8. The method of claim 1, wherein an upper teeth impression, a lower teeth impression, and a bite impression are scanned together.

9. The method of claim 8, further comprising digitally reversing data from the upper and lower impression scan data to make positive data.

10. The method of claim 9, wherein the digital reversing identifies inner surfaces of an impression material and extracting the inner surfaces using a largest connected component algorithm.

11. The method of claim 1, further comprising aligning data into a bite position using the impression material scanned.

12. The method of claim 1, further comprising digitally detailing the teeth data.

13. The method of claim 1, further comprising setting a final bite.

14. The method of claim 1, further comprising articulating the digital model.

15. A system to create a digital model of a patient's teeth from scanned data of improved quality, comprising:

a number of impression materials;

a dental tray adapted to hold the number of impression materials, the dental tray made of a tray material, each of the impression and tray materials having a respective radiopacity, at least one of the materials being formulated with a radiopaque agent such that the respective radiopacities of the materials approximately match each other;

a radiation source;

a scintillator to receive the radiation from the radiation source;

a radiation detector coupled to the scintillator;

a rotatable table positioned between the radiation source and the scintillator, the table being adapted to support the dental tray with the impression of the patient's teeth; and a computer coupled to the detector to generate the digital model with scanned data.

16. The system of claim 15, wherein the radiation source is an X-ray source.

17. The system of claim 15, wherein the radiation source is a computed tomography source.

18. The system of claim 15, wherein the rotatable table is adapted to support an upper teeth impression, a lower teeth impression and a bite impression.

19. The system of claim 15, further comprising a fabrication machine coupled to the computer to generate a plurality of appliances, wherein the appliances comprise polymeric shells having cavities and wherein the cavities of successive shells have different geometries shaped to receive and resiliently reposition the teeth from one arrangement to a successive arrangement.

20. The system of claim 15, wherein the dental tray comprises: a base having a plurality of prongs, the base having one or more openings to allow flowing of the dental impression material; a first wall extending from one side of the base, the first wall having one or more openings to allow flowing of the dental impression material; and at least one detachable portion formed on one end of one prong, the detachable portion being removable to shorten the prong length.

21. A method of improving the quality of scanned data from a dental impression made with a dental impression material in a dental tray, the tray made of a material, the method comprising formulating at least one of the dental impression material and the dental tray material with a radiopaque agent such that the respective radiopacities of the impression and tray materials approximately match each other.

22. The method of claim 21, wherein the radiopacity of the dental tray material is formulated to match the radiopacity of the dental impression material.

23. The method of claim 21, wherein the radiopacity of the dental impression material is formulated to match the radiopacity of the dental tray material.

24. The method of claim 21, wherein the radiopacity of the dental tray does not exceed the radiopacity of the dental impression material by more than 50%.

25. The method of claim 21, wherein the dental tray material is formed from a thermoplastic resin, and wherein radiopacity of the dental impression tray is adjusted by compounding a radiopaque agent into the thermoplastic resin.

26. The method of claim 21, wherein the radiopaque agent included in the dental tray material is any of barium sulfate, calcium carbonate, calcium chloride, sodium carbonate, magnesium sulfate, bismuth trioxide, bismuth subcarbonate, bismuth oxychloride and the heavy metal powder tungsten, gold platinum, or silver.

27. The method of claim 21, wherein the dental impression material is an elastomeric material, the elastomeric material being any of an irreversible hydrocolloid, a reversible hydrocolloid, a polysulfide, a polyether, a condensation reaction silicone, or an addition reaction silicone, and wherein the radiopacity of the impression material is adjusted by directly compounding a radiopaque agent into the impression material.

28. The method of claim 21, wherein the dental impression is an elastomeric material, the elastomeric material being any of an irreversible hydrocolloid, a reversible hydrocolloid, a polysulfide, a polyether, a condensation reaction silicone, or an addition reaction silicone, and wherein the radiopacity of the impression material is adjusted by applying a layer including a radiopaque agent onto the surface of the impression material.

29. The method of claim 21, wherein the radiopaque agent included in the dental impression material is any of barium sulfate, calcium carbonate, calcium chloride, sodium carbonate, magnesium sulfate, bismuth trioxide, bismuth subcarbonate, bismuth oxychloride and the heavy metal powder tungsten, gold, platinum, or silver.

30. A dental impression system configured to improve the quality of scanned data from a dental impression, the system comprising a dental impression material and a dental tray, the tray made of a material, each of the impression and tray materials having a respective radiopacity, at least one of the materials being formulated with a radiopaque agent such that the respective radiopacities of the materials approximately match each other.

31. The system of claim 30, wherein the radiopacity of the dental tray material is formulated to match the radiopacity of the dental impression material.

32. The system of claim 30, wherein the radiopacity of the dental impression material is formulated to match the radiopacity of the dental tray material.

33. The system of claim 30, wherein the radiopacity of the dental tray does not exceed the radiopacity of the dental impression material by more than 50%.

34. The system of claim 30, wherein the dental tray material is formed from a thermoplastic resin resin, and wherein radiopacity of the dental impression tray is adjusted by compounding a radiopaque agent into the thermoplastic resin.

35. The system of claim 30, wherein the radiopaque agent included in the dental tray material is any of barium sulfate, calcium carbonate, calcium chloride, sodium carbonate, magnesium sulfate, bismuth trioxide, bismuth subcarbonate, bismuth oxychloride and the heavy metal powder tungsten, gold platinum, or silver.

36. The system of claim 30, wherein the dental impression material is an elastomeric material, the elastomeric material being any of an irreversible hydrocolloid, a reversible hydrocolloid, a polysulfide, a polyether, a condensation reaction silicone, or an addition reaction silicone, and wherein the radiopacity of the impression material is adjusted by directly compounding a radiopaque agent into the impression material.

37. The system of claim 30, wherein the dental impression material is an elastomeric material, the elastomeric material being any of an irreversible hydrocolloid, a reversible hydrocolloid, a polysulfide, a polyether, a condensation reaction silicone, or an addition reaction silicone, and wherein the radiopacity of the impression material is adjusted by applying a layer including a radiopaque agent onto the surface of the impression material.

38. The system of claim 30, wherein the radiopaque agent included in the dental impression material is any of barium sulfate, calcium carbonate, calcium chloride, sodium carbonate, magnesium sulfate, bismuth trioxide, bismuth subcarbonate, bismuth oxychloride and the heavy metal powder tungsten, gold, platinum, or silver.

* * * * *